Figure 1:
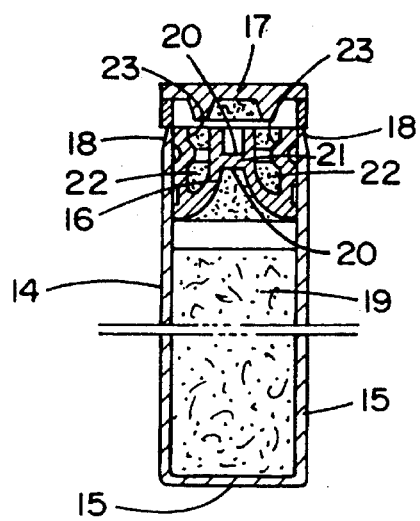

United States Patent [19]

Bigagli et al.

[11] Patent Number: 5,520,642
[45] Date of Patent: May 28, 1996

[54] TWO-COMPONENT DEVICE FOR THE ADMINISTRATION OF DRUGS

[75] Inventors: Roberto Bigagli; Gianni Grillenzoni; Mauro Landi; Augusto Arcari, all of Milan, Italy

[73] Assignee: Dibra S.p.A., Milan, Italy

[21] Appl. No.: 409,351

[22] Filed: Mar. 23, 1995

[30] Foreign Application Priority Data

Mar. 24, 1994 [IT] Italy .............................. MI94U0221 U

[51] Int. Cl.$^6$ .................................................. A61M 37/00
[52] U.S. Cl. .............................................. 604/88; 604/203
[58] Field of Search ............................... 604/89, 88, 187, 604/203, 200, 201, 218, 232, 905, 87, 86

[56] References Cited

U.S. PATENT DOCUMENTS

| | | | |
|---|---|---|---|
| 3,916,894 | 11/1975 | Cloyd | 604/203 |
| 4,014,330 | 3/1977 | Genese | 604/88 |
| 5,380,281 | 1/1995 | Tomellini et al. | 604/88 |

*Primary Examiner*—John D. Yasko
*Attorney, Agent, or Firm*—Bucknam and Archer

[57] ABSTRACT

This invention refers to a device for the administration of aqueous solutions or suspensions of drugs or diagnostic agents including, for instance, contrast media for X-ray, magnetic resonance and ultrasound procedures. In particular this invention refers to a two-component device, substantially constituted by: a) a piston-container, which is prefilled with an injectable solution/suspension, and sealed by a stopper-plunger, b) a housing-barrel, provided with collecting and administration systems. Said components a) and b) are combined together only when used, ensuring the preparation sterility.

4 Claims, 1 Drawing Sheet

TWO-COMPONENT DEVICE FOR THE ADMINISTRATION OF DRUGS

FIELD OF THE INVENTION

This invention refers to a device for the administration of aqueous solutions or suspensions of drugs or diagnostic agents including, for instance, contrast media for X-ray, magnetic resonance and ultrasound procedures. In particular this invention refers to a two-component device, substantially constituted by: a) a piston-container, which is prefilled with an injectable solution/suspension, and sealed by a stopper-plunger, b) a housing-barrel, provided with collecting and administration systems. Said components a) and b) are combined together only when used, ensuring the preparation sterility.

BACKGROUND OF THE INVENTION

Devices apparently comparable to that of this invention are known in this field. Among the most interesting documents we can cite for instance those reported in the following documents: WO 9218178, EP-A 0206971, U.S. Pat. No. 3,994,296, FR-A 2262535, DE-U 9003505, FR-A 1551012.

Nevertheless none of them succeeded in solving the most important problems related to this kind of device, such as for instance:

1) a perfect sealing of the stopper-plunger, ensuring a good sliding capacity;
2) a perfect coupling system of the two components which is both simple (for instance the screw type is excluded) and efficient in order to allow the possible sliding back of the piston-container during the use, when needed;
3) the need of avoiding that the sharp end of the housing-barrel collecting system (the collecting needle tip) accidentally comes into contact with the operator.

In particular WO 9218178, which suggests one of the simplest and most interesting solution, was not able to solve points 1) and 2) in an acceptable way.

SUMMARY OF THE INVENTION

Figure 3:
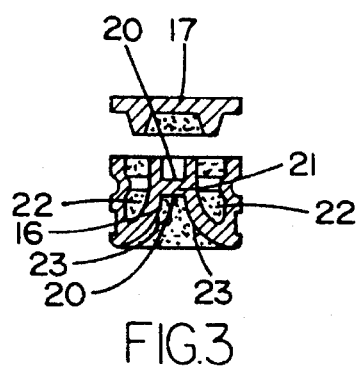
Figure 2:
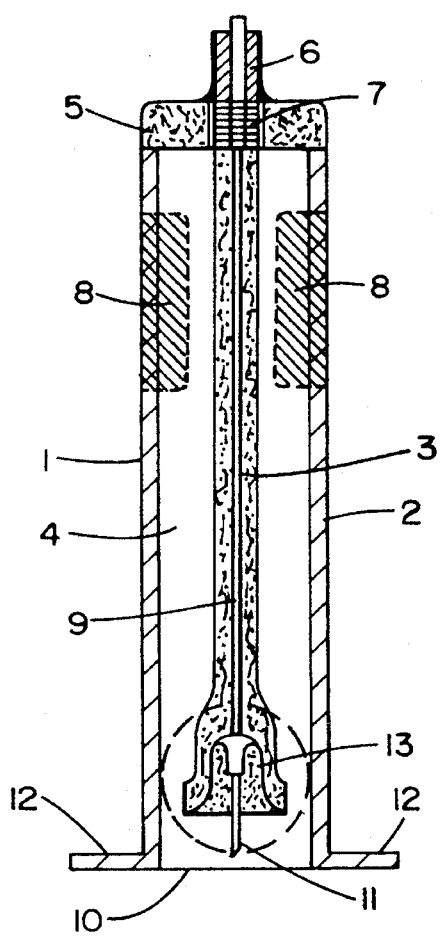
Figure 4:
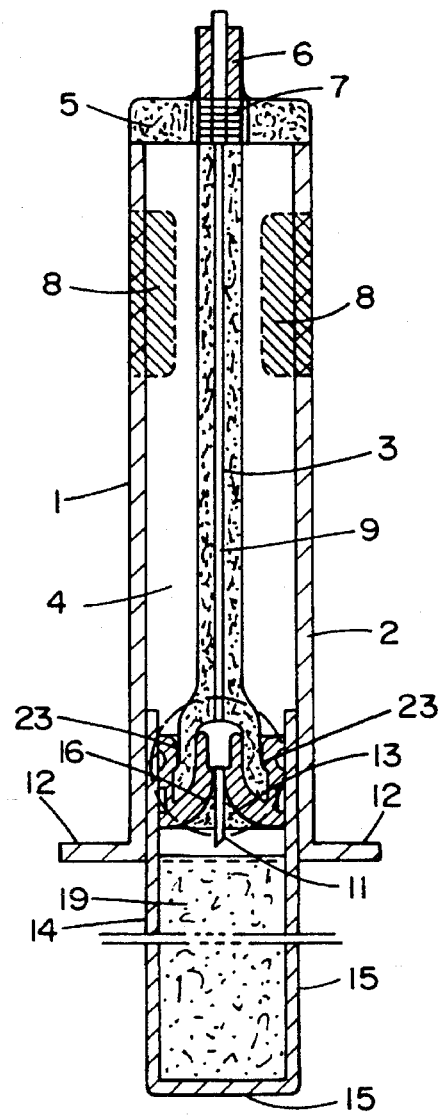

The object of this invention is going to be described as a non-limiting example, with reference to the annexed drawings (FIGS. 1–4), wherein:

FIGS. 1 and 2 are axial sections of the two elements constituting the claimed device (piston-container and housing-barrel), FIG. 3 details the structure of the group responsible for the strong coupling of said housing-barrel with said piston-container, that is to say the stopper-plunger; the same FIG. 3 shows as a matter of example, a possible stopper-gasket ensuring the external sealing of the piston-container;

FIG. 4 shows the elements assembled in the position of use.

The housing-barrel (1) (FIG. 2) is preferably made of plastic for medical or pharmaceutical uses. This material which has to sustain, without deformation or damages, the commonly used sterilization conditions (for instance autoclave) can also be made of totally or nearly totally biodegradable material (in any case said housing-barrel (1) can also be made of glass). It generally has a tubular structure and is substantially constituted by an external jacket (2) and an inner jacket (3). These jackets (2) and (3) define an annular cavity (4) closed at one end by a pierced sealing (5) to which an external joint formation (6) is applied for the connection, for instance, of a hypodermic needle (not drawn in the figures). This sealing (5) can also be provided with another inner joint unit (7), to which the inner jacket (3) is connected in case the inner jacket (3) has to be removed after the use, to recover the part of the housing-barrel which did not come into contact with the administered liquid. In this case, the removal is feasible thanks to suitable side openings (8) in the external jacket (2) (as from FIGS. 2 and 4, shaded parts), which allow an easy access to the inside of the housing-barrel (1).

Inside the inner jacket (3), preferably in central axial position, a needle (9) is housed, which extends for the entire housing-barrel (1) length and ends, opened end (10), with a sharp tip (11). This sharp tip (11) must not protrude from (1) and therefore must be in line (or preferably slightly inside) with respect to the opened extremity (10). The needle (9) is preferably made of steel, but plastic needles can be equally used, with obvious benefits from the environmental and economical point of view, when biodegradable plastic is used.

At its opened end (10), the external jacket (2), is equipped with an external flange (12) acting as handle for the use of the device.

Through the pierce in the sealing (5), the cavity is directly connected with the external joint (6). At the opposed end (opened end (10)) the needle (9) is surrounded by a coupling group (13) (FIG. 2 circular shaded part), responsible for the connection and the coupling to the stopper-plunger of the piston-container. The coupling group (13) is bell shaped and made of the same material as the inner jacket (3), forming a unique block with the same.

The other element of the device, that is to say the piston-container (14) (FIG. 1) is preferably constituted by a cylindrical body (15) closed at one end, made of glass or plastic for pharmaceutical use, which contains the drug or the contrast medium solution/suspension to be injected (19). The container (15) is sealed at the mouth by a mobile device (16) (stopper-plunger), acting as a sealing element, and as a plunger able to slide inside the container (15).

The stopper-plunger (16) is preferably made of soft rubber (for instance bromobutyl, chlorobutyl rubber or analogous mixtures), or of other elastomeric materials (possibly even autolubricating). In any case it is designed to ensure an excellent sliding inside the container (15), supplying at the same time a perfect sealing, during the sterilization phase of the packaging, the stocking period and also during the use.

After the filling with the desired pharmaceutical composition and the sealing with the stopper-plunger (16) (this operation is preferably carried out under slight depression), the piston-container (14) is sealed with a suitable and tightly sealing gasket (17). This gasket (17) can be fixed in different ways, for instance with easily removable blocking capsules (which are not shown in the figures), for instance flip-off capsules.

Of course these devices require for instance suitable possibilities of seaming (18) to the container mouth (15), which should be accordingly designed.

The stopper-plunger (16) is crossed by an axial hole (20) closed by a diaphragm (21) which will be perforated by the sharp tip of the needle (9).

The most remarkable feature of the solution according of this invention is that in the upper part of the stopper-plunger (16), that is to say the external one, a cavity (22) is housed the shape of which is complementary to the coupling group (13) of the inner jacket (3) of the housing-barrel (1). This cavity (22), as for FIG. 4, is responsible for the coupling of the two components of the device of this invention. These two components are usually packaged as sterile assembling kit ready for the use.

During the use the stopper-gasket (17) is removed by releasing the blocking and sealing systems associated to it (which are not illustrated).

Then the piston-container (14) is connected to the opened end (10) of syringe (1) following the conditions of FIG. 4, that is to say the introduction of the peripheral wall of the container (14) into the annular cavity (4) defined by the jackets (2) and (3) of the barrel (1). This result can be achieved by connecting the stopper-plunger (16) to the end (13) of the inner jacket (3) and by favouring the introduction of this end (13) into the cavity (22) in order to accomplish a shape coupling between the two parts.

This result is generally achieved due to the penetration and the snapping shut of the bell-shaped coupling group (13) (male part) inside the complementary cavity (22) (female part). This performance is easily carried out thanks to the general softness of the plunger (16) material; in fact the locking lip (23) which defines the narrow part of the cavity mouth (22) appears to be elastically yielding with respect to the action of penetration of the coupling group (13). On the other hand, the inner/inferior shape of the lip (23) has been designed to firmly block the coupling group (13) once the penetration has been accomplished, avoiding an easy release of the group with a consequent release of the two parts.

In this way an automatic snapping shut coupling operation with a precise coupling ratio of complementary shape can be performed, as shown in FIG. 4.

Due to this coupling, the needle (9), in particular its sharp tip (11), cracks the diaphragm (21) so that the inner cavity of the piston-container (14) comes into contact with the inside of the collecting needle (9).

Now, a hypodermic needle can be, for instance, inserted on the handle (6) and, after having seized the flange (12) of the syringe (1) with two fingers, the pressure of the thumb on the container (15) base allows the introduction of the same inside the annular cavity (4) of the housing-barrel (1) with the consequent retraction of the plunger (16) into the container (15). This produces the outflow of the liquid content (19) through the needle (9) and therefore through the hypodermic needle placed on the handle (6).

The firm coupling of the stopper-plunger (16) to the coupling device (13) as previously described allows in any case the possible retraction of the container (15), when necessary, for instance during an injection. In addition the type of material constituting the stopper-plunger (16) allows an excellent sealing action in the connection between container (15) and needle (9). All these characteristics do not dampen the sliding capacity of the stopper-plunger (16), favouring a remarkably smooth performance of the administration procedure.

Finally, we must not discard the environmental impact. The possible use of biodegradable materials, as well as the possibility of an easily removable inner jacket (3) after the use, and the reuse of the same external container syringe for a high number of procedures, highly contribute to a production decrease of waste in the field of disposable injectable products.

We claim:

1. A device for the administration of aqueous solutions and suspensions of drugs and diagnostic agents comprising a first element (14) and a second element (1), to be coupled one to the other when used, wherein:

the first element (14) comprises a container for fluids (15), a stopper-plunger (16) sealing said container, said stopper-plunger being opened to the flow of a fluid through a piercable baffle (21) and being slidable inside said container (15), in order to produce the outlet of the fluid contained in it, the second element (1) is a housing-barrel comprising an external jacket (2) and an inner jacket (3), said inner jacket (3) being equipped with a collecting system (11) and an administration system (9), said jacket (3) being joinable to the stopper-plunger (16), piercing it in said piercable baffle (21) and allowing the motion of said plunger inside the container (15), producing the outlet of the fluid contained in it, said jacket (3) and said stopper-plunger (16), being respectively associated to complementary male part (13) and female part (22) of a coupling system, said coupling system performing a mutual strong coupling when said first and the second element, (14) and (1) respectively, are combined together so that the container (15) can be retracted during use, said collecting system and said administration system being connected to said inner jacket (3) and comprising a needle (9) ending with a sharp tip (11), said sharp tip being capable of piercing said stopper-plunger (16) through said baffle (21), said tip (11) being surrounded by said male and female coupling system, and not protruding from said second element (1), and in addition, said housing barrel (1) having an open end (10), said male and female coupling system (13) and (22) and said sharp tip (11) being housed inside said housing barrel (1), and being slightly retracted with respect to said open end (10), in order to avoid any contact with the operator, further said male coupling part (13) being bell-shaped, said complementary female part (22) of said stopper-plunger (16) being provided with a locking lip (23) to firmly block the coupling of said parts (13) and (22), and to avoid easy release of said parts, said external jacket (2) and said inner jacket (3) defining a cavity (4), a sealing device (5) for closing said cavity, said sealing device (5) being provided with an inner joint unit (7), said inner jacket (3) of said housing barrel (1) is removably fixed to said joint unit (7), thus allowing the after-use recovery and the re-use of that part of said housing-barrel (1) which does not come into contact with the administered fluid, and in addition, the external jacket (2) is provided with side openings (8), for allowing access in the interior of said housing barrel (1) to remove said inner jacket (3).

2. The device according to claim 1 wherein the first element (14) and said housing barrel (1) are cylindrically shaped and the complementary coupling parts (13) and (22) are placed in axial position with respect to said element (14) and said housing barrel (1).

3. The device according to claim 1 wherein:

said needle (9) is made of steel or plastic, said stopper plunger (16) is made of an elastomeric material selected from the group consisting of bromo- or chlorobutyl rubber whereby high sealing and sliding performance are achieved, said element (14) being made of glass and said housing barrel (1) being made of plastic material.

4. The device according to claim 3 wherein said plastic material is biodegradable.

* * * * *